United States Patent [19]
Haas et al.

[11] 3,973,024
[45] Aug. 3, 1976

[54] ANALGESIC AND ANTI-INFLAMMATORY ANILINO-PHENYLACETIC ACID-(2,3 OR 4 PYRIDYL)-METHYL ESTERS AND DERIVATIVES

[75] Inventors: Georges Haas, Oberwil; Alfred Sallmann, Bottmingen, both of Switzerland

[73] Assignee: Ciba-Geigy Corporation, Ardsley, N.Y.

[22] Filed: Apr. 28, 1975

[21] Appl. No.: 572,555

Related U.S. Application Data

[62] Division of Ser. No. 387,405, Aug. 10, 1973, Pat. No. 3,897,437.

[30] Foreign Application Priority Data

Aug. 16, 1972 Switzerland.................. 12128/72

[52] U.S. Cl. .................................................. 424/263
[51] Int. Cl.[2].......................................... A61K 31/44
[58] Field of Search ..................................... 424/263

[56] References Cited
UNITED STATES PATENTS
3,557,129  1/1971  Karmas ........................... 260/295 R OTHER PUBLICATIONS
Roberts et al., Basic Principles of Organic Chem. Benjamin Publishers p. 806 (1965).

*Primary Examiner*—Norman A. Drezin
*Attorney, Agent, or Firm*—Joseph G. Kolodny; John J. Maitner; Theodore O. Groeger

[57] ABSTRACT

Basic esters and acid addition salts thereof of substituted o-anilino-phenylacetic acids with pyridinols or pyridine-alkanols have anti-inflammatory and analgesic activity; they are active ingredients of pharmaceutical compositions and can be used for the relief and removal of pain as well as for the treatment of rheumatic, arthritic and other inflammatory complaints; an illustrative example is [o-(2,6-Dichloro-anilino)-phenyl]-acetic acid (2-pyridyl)-methyl ester.

10 Claims, No Drawings

ANALGESIC AND ANTI-INFLAMMATORY ANILINS-PHENYLACETIC ACID-(2,3 OR 4 PYRIDYL)-METHYL ESTERS AND DERIVATIVES

This application is a division of application Ser. No. 387,405, filed Aug. 10, 1973, now U.S. Pat. No. 3,897,437.

The present invention relates to new substituted phenylacetic acid esters of the general formula I

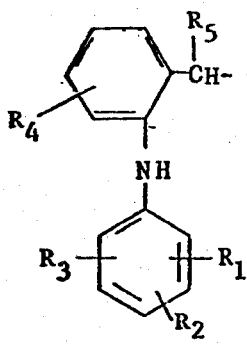

(I)

in which $R_1$ represents lower alkyl, lower alkoxy, halogen up to atomic number 35 or trifluoromethyl, $R_2$ represents hydrogen or a substituent corresponding to the definition of $R_1$, $R_3$ represents hydrogen, lower alkyl, lower alkoxy or halogen up to atomic number 35, $R_4$ represents hydrogen, lower alkyl, lower alkoxy, halogen up to atomic number 35 or trifluoromethyl, $R_5$ represents hydrogen, lower alkyl or benzyl, A represents a direct bond, lower alkylene or lower alkylidene and Py represents an optionally lower alkyl-substituted or lower alkoxy-substituted pyridyl group or the N-oxide thereof, acid addition salts thereof, processes for their manufacture, pharmaceutical material compositions which contain these compounds, and their use.

The term "lower" which is used throughout this specification in connection with organic radicals, groups or compounds indicates that organic radicals, groups or compounds thus qualified contain up to 7, preferably up to 4, carbon atoms.

A group $R_1$–$R_5$, and a substituent in the group Py, when representing a lower alkyl radical, is above all methyl or ethyl and also, for example, straight-chain or branched propyl, butyl, pentyl, hexyl and heptyl whilst when representing a lower alkoxy radical it is above all methoxy or ethoxy and also, for example, straight or branched propoxy, butoxy, pentoxy, hexoxy and heptoxy. If $R_1$–$R_4$ represents a halogen atom, it is preferably chlorine and also fluorine and bromine. A lower alkylene or lower alkylidene group is, for example, a divalent group derived from the above mentioned lower alkyl groups such as, for example, methylene, ethylene, ethylidene, 1,2- or 1,3-propylene or propylidene.

The symbol Py is an optionally N-oxidised 2-, 3- or 4-pyridyl group which is substituted by one or more, preferably one or two, of the above mentioned lower alkyl or lower alkoxy radicals or, most preferably, is unsubstituted.

Examples of such groups are 2-, 3- or 4-pyridyl, 3-, 4-, 5- or 6-methyl-2-pyridyl, 2-, 4-, 5- or 6-methyl-3-pyridyl, 2- or 3-methyl-4-pyridyl, 3-, 4-, 5- or 6-methoxy-2-pyridyl, 2-, 4-, 5- or 6-methoxy-3-pyridyl, 2- or 3-methoxy-4-pyridyl and the corresponding N-oxides.

Acid addition salts are, preferably, pharmaceutically useful non-toxic acid addition salts, for example salts with inorganic acids, such as with a hydrogen halide acid, for example hydrochloric acid or hydrobromic acid, with an oxygen acid, for example sulphuric acid, phosphoric acid, nitric acid or perchloric acid, or with an organic acid, especially an organic carboxylic acid or sulphonic acid, for example a lower alkanemonocarboxylic acid or lower alkanedicarboxylic acid or lower alkenemonocarboxylic acid or lower alkenedicarboxylic acid which is optionally substituted, for example by hydroxyl, oxo or phenyl, for example formic acid, acetic acid, propionic acid, succinic acid, glycolic acid, lactic acid, malic acid, tartaric acid, citric acid, hydroxymaleic acid, pyruvic acid or phenylacetic acid, with a benzoic acid which is optionally substituted, for example by amino or hydroxyl, for example benzoic acid, 4-aminobenzoic acid, anthranilic acid, 4-hydroxybenzoic acid, salicylic acid, aminosalicylic acid and also ascorbic acid, embonic acid or nicotinic acid, and with an optionally substituted lower alkanesulphonic acid or lower alkenesulphonic acid, such as methanesulphonic acid, ethanesulphonic acid, hydroxyethanesulphonic acid or ethylenesulphonic acid, or with a benzenesulphonic acid which is optionally substituted, for example benzenesulphonic acid, halogenobenzenesulphonic acid or toluenesulphonic acid.

The compounds according to the invention possess valuable pharmacological properties, especially an anti-inflammatory and analgesic activity, and a favourable therapeutic index. The anti-inflammatory activity is evidenced, for example, on rats in the kaolin paw oedema test according to L. Riesterer and R. Jaques, Helv.physiol. pharmakol. Acta 25, 156 (1967), in which the compounds according to the invention possess a detectable action on peroral administration of about 1 to 100 mg/kg.

The analgesic effects can be demonstrated, for example, by means of the writhing test on mice, for example according to the method developed by Siegmund et al., Proc. Soc. Exptl. Biol.Med., volume 95, page 729 (1957), at oral doses of about 30 to about 100 mg/kg.

The compounds of the present invention can therefore be used as analgesic agents, especially as anti-inflammatory agents, above all for the treatment of arthritic symptoms. Furthermore, they are suitable for use as UV-absorbers for cosmetic purposes, for example as a constituent for anti-sunburn creams, since they absorb the harmful reddening rays of 290–300 m$\mu$ whilst they transmit the desired bronzing rays of above 315 m$\mu$. Furthermore, they can be used as intermediate products in the manufacture of other pharmacologically active, valuable compounds.

Preferred compounds of the invention are those of the formula I, wherein $R_1$ is in the 2-position of the anilino group and represents chlorine or methyl, $R_2$ is in the 3- or 6-position and is hydrogen, chlorine or methyl and $R_3$ represents hydrogen or, if $R_2$ is in the 6-position, also represents a 3-methyl group. In the preferred compounds, $R_4$ is in the 5-position of the phenylacetic acid grouping and represents hydrogen or chlorine and $R_5$ preferably represents hydrogen.

The compounds in which A is methylene, ethylene or propylene and Py is an unsubstituted 2-, 3- or 4-pyridyl group are also preferred. If A represents the direct bond, Py is preferably the 3-pyridyl radical.

Further preferred compounds of the invention are the pharmacologically tolerable acid addition salts of the above preferred compounds of the formula I.

The following compounds are preferred:

[o-(2,6-dichloro-anilino)-phenyl]-acetic acid-3-(4-pyridyl)-propyl ester,
[o-(2,6-dichloro-anilino)-phenyl]-acetic acid-2-(2-pyridyl)-ethyl ester,
[o-(2-methyl-6-chloro-anilino)-phenyl]-acetic acid-(2-pyridyl)-methyl ester,
[o-(2-methyl-6-chloro-anilino)-phenyl]-acetic acid-(3-pyridyl)-methyl ester.

Particularly preferred compounds are:

[o-(2,6-dichloro-anilino)-phenyl]-acetic acid-(2-pyridyl)-methyl ester, [o-(3-methyl-2,6-dichloro-anilino)-phenyl]-acetic acid-(2-pyridyl)-methylester,
[o-(2,6-dichloro-anilino)-phenyl]-acetic acid-(3-pyridyl)-methyl ester,
[o-(2,6-dichloro-anilino)-phenyl]-acetic acid-(4-pyridyl)-methyl ester.

The compounds according to the invention can be manufactured in a manner which is in itself known. For example, an acid of the formula II

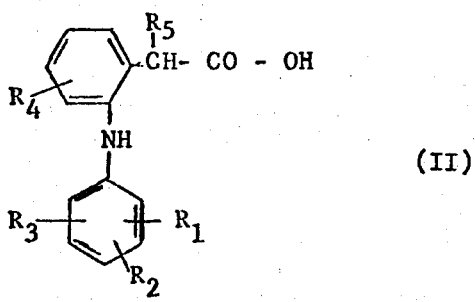

a salt or a reactive functional derivative thereof can be reacted with a hydroxy compound of the formula HO—A—Py (III) or a reactive functional derivative thereof, and of desired, within the scope of the end products a resulting compound can be converted into another compound of the invention.

The reaction of the acid of the formula II with the hydroxy compound of the formula III preferably takes place by heating to 60°–150°C in the presence of an acid catalyst, such as a Lewis acid, for example boron trifluoride, or of a proton acid, for example a hydrogen halide acid, such as hydrochloric acid, an oxygen acid, such as sulphuric acid, or an organic sulphonic acid, such as a lower alkanesulphonic acid or benzenesulphonic acid which is optionally substituted, for example by methyl, halogen or phenyl, for example methanesulphonic acid or toluenesulphonic acid. A carboxylic acid, such as the compound of the formula II itself, can also be used as catalyst. The reaction is advantageously carried out in a solvent, for example in an excess of the compound of the formula III, optionally in the presence of a diluent, such as an ether-like solvent, for example dioxane or ethylene glycol dimethyl ether, or a hydrocarbon, such as toluene.

The water which forms during the esterification is advantageously removed continuously, for example by distillation, preferably as an azeotropic mixture. However, it is also possible to carry out the esterification under mild conditions, e.g. at 0°–30°C, in the presence of a hydrophilic agent, for example trifluoroacetic anhydride, or also with phosphorus oxychloride or a sulphonic acid chloride in a non-acylatable amine, for example pyridine. It is also possible to react an acid of the formula II with a functional derivative of a hydroxy compound of the formula II e.g. with an acetal. Particularly suitable acetals on account of their high reactivity are those which are derived from a N,N'-di-lower alkyl-lower alkane acid amide, for example dimethyl formamide [cf. Eschenmoser et al, Ang. Chem. 75, 296 (1963)]. The esterification of the acid of the formula II with such an acetal is preferably carried out in an inert solvent, for example in an ether-like solvent, e.g. in a di-lower alkyl ether, for example diethyl ether, in an optionally chlorinated aliphatic or aromatic hydrocarbon, such as in benzene, toluene or methylene chloride, in a nitrile, e.g. a lower alkanoic acid nitrile, for example acetonitrile, or in the amide used for the acetalisation, e.g. dimethyl formamide. According to a preferred embodiment, the acetal is manufactured in situ by treating the acid of the formula II with the hydroxy compound of the formula III, together with an acetal formed from a N,N-di-lower alkyl-lower alkanoic acid amide and a sterically hindered lower alkanol, for example together with N,N-dimethylformamidedineopentyl-acetal, [cf. Eschenmoser et al, Ang. Chem. 75, 1176–1177 (1963)]. This reaction is also preferably carried out in one of the abovementioned solvents.

The salts of the acids of the formula II are suitable for reaction with reactive esters of hydroxy compounds of the formula III. Such esters are for example the esters with strong acids, such as hydrogen halide acids, for example with hydrochloric acid or hydrobromic acid, or with organic sulphonic acids such as with lower alkanesulphonic acids or benzenesulphonic acids which are optionally substituted, for example by halogen, lower alkyl, nitro or phenyl, for example methanesulphonic acid, benzenesulphonic acid, toluenesulphonic acid or p-chlorobenzenesulphonic acid, or with strong carboxylic acids, for example trifluoroacetic acid. These esters are preferably reacted with a salt, for example a metal salt, such as an alkali metal salt or alkaline earth metal salt, for example the sodium salt or calcium salt, of the acid of the formula II. Furthermore it is also possible to use salts with non-acylatable organic bases, for example with tertiary lower alkylamines such as with diisopropylethylamine, or with a nitrogen-containing heterocyclic compound, such as pyridine. The reaction is preferably carried out in a solvent, for example in water, in an ether-like solvent, for example in a di-lower alkyl ether, e.g. diethyl ether, in a cyclic ether, e.g. dioxane, or, particularly preferably, in a liquid amide, e.g. a N,N-di-lower alkyl-lower alkanoic acid amide, for example dimethyl-formamide, or a di-lower alkylamide of phosphoric acid, e.g. hexamethylphosphoric acid triamide.

Particularly reactive functional derivatives of the acid of the formula II are the halides, so that the esterification can therefore be carried out under mild conditions. Preferably the process is carried out in inert solvents, for example in those cited herein above.

The esters of the acids of the formula II can also be reacted with the hydroxy compounds of the formula III. This transesterification is advantageously carried out in such a manner that the alcohol split off from the starting ester of the acid of the formula II is removed continuously from the reaction mass, for example by distilling it off, if the alcohol has a lower boiling point than the reactants. The transesterification is carried out in the melt, i.e. without solvent or in the presence of an inert solvent or an excess of the hydroxy compound of the formula III. The reaction can be speeded up by using acid catalysts, for example those described hereinbefore. Still more effective are as a rule basic catalysts, e.g. an alcoholate, for example an alkali metal alcoholate, such as a sodium alcoholate, of the hydroxy compound of the formula III.

The transesterification proceeds particularly smoothly if reactive esters of acids of the formula II are used, e.g. the p-nitrophenyl and the cyanomethyl esters which are described in German Offenlegungsschrift No. 2,144,641, together with an alkali alcoholate of a hydroxy compound of the formula III. One modification of the transesterification method consists in using instead of the hydroxy compound of the formula III a carboxylic acid ester thereof.

Suitable functional derivatives of carboxylic acids of the formula II are also active amides thereof, for example the imidazolides and s-triazolides which react readily with the hydroxy compounds of the formula III using alkali catalysts, cf. H. A. Staab et al, Ber. 95, 1275 and 1284 (1962).

According to a further modification of the process, a compound of the formula I, wherein $R_5$ represents a hydrogen atom, can be obtained if nitrogen is eliminated from a compound of the formula IV

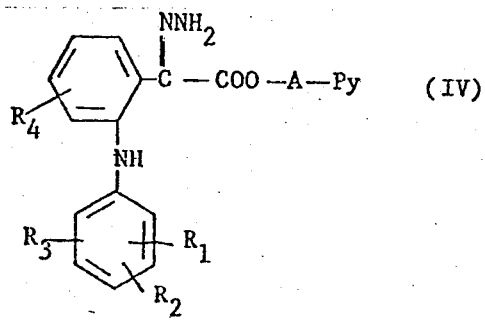

and a resulting compound is converted, if desired, within the scope of the end products, into another compound of the invention.

The elimination of the nitrogen can be carried out according to the Wolff-Kishner method by heating the compound of the formula IV in the presence of a strong base. The base used is advantageously an alcoholate, for example an alkali metal alcoholate, e.g. the sodium alcoholate, of the hydroxy compound of the formula III. The reaction is advantageously carried out in a higher-boiling solvent, for example in an ether-like solvent, e.g. diethylene glycol dimethyl ether.

In a resulting compound wherein Py is an optionally lower alkyl-substituted or lower alkoxy-substituted pyridyl group, the latter can be converted into a corresponding N-oxidised pyridyl group in a manner which is in itself known, for example by treatment with a N-oxidising agent. Examples of N-oxidising substances are hydrogen peroxide and per-acids, such as lower alkanepercarboxylic acids, for example peracetic acid, which can be used in water or in a lower alkanoic acid, such as acetic acid. However, preferred N-oxidising agents are aromatic percarboxylic acids, such as optionally halogen-substituted benzenepercarboxylic acids, for example perbenzoic acid or m-chloroperbenzoic acid, and also monoperphthalic acid, which can advantageously be employed in inert organic solvents, for example in ether-like liquids, such as di-lower alkyl ethers, for example diethyl ether, or optionally halogenated hydrocarbons, such as benzene or chloroform.

In a resulting compound of the formula I wherein Py represents a N-oxidised, optionally lower alkyl-substituted or lower alkoxy-substituted pyridyl group, the latter can be converted into a corresponding free pyridyl group in a manner which is in itself known, for example by reduction. The reduction can be carried out with hydrogen which is activated catalytically, for example with a transition metal catalyst, such as a nickel, palladium or platinum catalyst, preferably in a solvent, for example in a lower alkanol, for example methanol or ethanol. However, it is also possible to use chemical reducing agents, for example complex hydrides of boron, for example diborane or sodium borohydride, preferably in an ether-like liquid, such as in a di-lower alkyl ether, for example diethyl ether, and also sulphur or its derivatives of a low level of oxidation, for example sodium dithionite or sulphur dioxide.

The reactions mentioned can be carried out in the usual manner, in the presence or absence of diluents, condensation agents and/or catalytic agents, at lowered, normal or elevated temperature, and optionally in a closed vessel and/or under an inert gas atmosphere. The conversions of final substances into other final substances can furthermore be carried out in any desired sequence.

Depending on the process conditions and starting substances, the final substances are obtained in the free form or in the form of their salts also including in the invention. Free compounds obtained can be converted into salts in a manner which is in itself known, for example by reaction with organic or inorganic acids, especially the initially mentioned acids, which are suitable for forming therapeutically usuable salts. Resulting salts with acids can be converted into the free compounds in a manner which is in itself known, for example with alkalis or with basic ion exchangers.

Salts can also be used for purifying the new compounds, for example by converting the free compounds into their salts, isolating these and reconverting them to the free compounds. Because of the close relationships between the new compounds in the free form and in the form of their salts, what has been said previously and is stated hereinafter in this specification with reference to the free compounds refers also to the corresponding salts, as the case may be, in respect of sense and purpose.

Depending on the choice of the starting substances and procedures, and depending on the number of the asymmetrical carbon atoms, the new compounds can be in the form of optical antipodes, racemates or isomer mixtures (racemate mixtures).

Resulting isomer mixtures (racemate mixtures) can be resolved into the stereoisomeric (diastereomeric) pure racemates in a known manner on the basis of the physicochemical differences of the constituents, for example by chromatography and/or fractional crystallisation.

Resulting racemates can be resolved into the diastereomers according to known methods, for example by recrystallisation from an optically active solvent, with the aid of micro-organisms, or by reaction with an optically active acid which forms salts with the racemic compound and separation of the salts obtained in this manner, for example on the basis of their different solubilities, and the antipodes can be liberated from the diastereomers by the action of suitable agents. Examples of particularly customary optically active acids are the D- and L-forms of tartaric acid, di-o-toluyltartaric acid, malic acid, mandelic acid, camphorsulphonic acid or quinic acid. Advantageously, the more active or less toxic of the two antipodes is isolated.

However, it is also possible to manufacture pure isomers, racemates or optical antipodes by starting from the appropriate starting substances in the form of their pure isomers, racemates or optical antipodes.

The invention also relates to those embodiments of the process according to which a compound obtainable as an intermediate product at any stage of the process is used as the starting material and the missing process steps are carried out, or in which a starting substance is formed under the reaction conditions, or in which a reaction component is in the form of its salt, if appropriate.

Appropriately, those starting substances are used for carrying out the reactions according to the invention which lead to the groups of final substances which initially have been mentioned particularly, and especially which lead to the final substances which have been especially described or singled out.

The starting substances of the formula II, their salts and functional derivatives, are known or, if they are new, can be manufactured according to methods which are in themselves known.

The starting substances of the formula IV can be obtained, for example, by reacting a glyoxylic acid derivative of the formula V

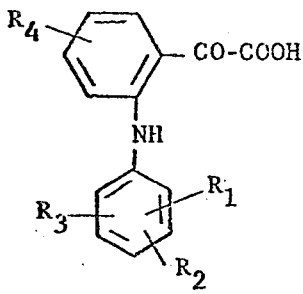

(V)

an ester thereof, such as a lower alkyl ester, or a salt thereof, such as an alkali metal salt, with a hydroxy compound of the formula III or a reactive functional derivative thereof, under the conditions indicated above for the manufacture of compounds of the formula I, and allowing the ester thereby obtained to react with hydrazine. The hydrazine can also be employed in the form of a salt or hydrate. The reaction can be carried out in a solvent, for example in water, a lower alkanol, such as ethanol, or an ether-like solvent, such as diethylene glycol dimethyl ether.

The new compounds of the present invention can be administered perorally, rectally or parenterally. They can also be used externally, incorporated in ointment bases or sun oil bases. Suitable unit dosage forms, such as dragées, tablets, suppositories or ampoules preferably contain, as the active substance, 10–500 mg of a compound according to the invention. In unit dosage forms for peroral use, the content of active substance is preferably between 10% and 90%. To manufacture such unit dosage forms the active substance is combined, for example, with solid pulverulent excipients, such as lactose, sucrose, sorbitol or mannitol, starches, such as potato starch, corn starch or amylopectin, or laminaria powders or citrus pulp powders, cellulose derivatives or gelatine, optionally with the addition of lubricants, such as magnesium stearate or calcium stearate or polyethylene glycols, to give tablets or to give dragée cores. The latter are coated, for example, with concentrated sugar solutions which can, for example, additionally contain gum arabic, talc and/or titanium dioxide, or with a lacquer dissolved in readily volatile organic solvents or solvent mixtures. Dyestuffs can be added to these coatings, for example to characterise various doses of active compound. Further suitable oral unit dosage forms are push-fit capsules of gelatine and soft, sealed capsules of gelatine and a plasticiser, such as glycerine. The former preferably contain the active substance as granules mixed with lubricants, such as talc or magnesium stearate, and optionally with stabilisers, such as sodium metabisulphite ($Na_2S_2O_5$) or ascorbic acid. In soft capsules, the active substance is preferably dissolved or suspended in suitable liquids, such as liquid polyethylene glycols, and again stabilisers can be added. Suitable unit dosage forms for rectal use are, for example, suppositories, which consist of a combination of an active substance with a suppository base composition which is based on natural or synthetic triglycerides (for example cacao butter), polyethylene glycols or suitable higher fatty alcohols, and gelatine rectal capsules which contain a combination of the active substance with polyethylene glycols. Ampoule solutions for parenteral administration, especially intramuscular or intravenous administration, contain, for example, the compound of the general formula I or a N-oxide thereof in a concentration of, preferably, 0.5–5%, as an aqueous dispersion prepared with the aid of customary solvents and/or emulsifiers and optionally stabilisers, or as an aqueous solution of a pharmaceutically tolerated, water-soluble acid addition salt of the compound.

Further examples of forms for parenteral administration are lotions, tinctures and ointments, prepared with the customary auxiliaries, for percutaneous application.

The following instructions are intended to explain in more detail the manufacture of the various forms for administration:

a. 1,000 g of active substance, for example [o-(2,6-dichloroanilino)-phenyl]-acetic acid (2-pyridyl)-methyl ester are mixed with 550 g of lactose and 292 g of potato starch and the mixture is moistened with an alcoholic solution of 8 g of gelatine and is granulated through a sieve. After drying, 60 g of potato starch, 60 g of talc and 10 g of magnesium stearate and 20 g of highly disperse silicon dioxide are mixed in and the mixture is pressed to give 10,000 tablets each weighing 200 mg and each containing 100 mg of active substance; the tablets can, if desired, be provided with breaking grooves for finer selection of the dosage.

b. 200 g of active substance, for example [o-(2,6-dichloroanilino)-phenyl]-acetic acid (2-pyridyl)-methyl ester are well mixed with 16 g of corn starch and 6 g of highly disperse silicon dioxide. The mixture is moistened with a solution of 2 g of stearic acid, 6 g of ethylcellulose and 6 g of stearin in approx. 70 ml of isopropyl alcohol and granulated through a sieve III (Ph.Helv.V). The granules are dried for approx. 14 hours and then beaten through a sieve IIIa. Thereafter they are mixed with 16 g of talc and 2 g of magnesium stearate and pressed to give 1,000 dragée cores. These are coated with a concentrated syrup of 2 g of shellac, 7.5 g of gum arabic, 0.15 g of dyestuff, 2 g of highly disperse silicon dioxide, 25 g of talc and 53.35 g of sugar, and are dried. The resulting dragées each weigh 360 mg and each contain 200 mg of active substance.

c. 50.0 g of [o-(2,6-dichloroanilino)-phenyl]-acetic acid (4-pyridyl)-methyl ester are dissolved in the calculated amount of 1 N-hydrochloric acid and the solution is made up to 2,000 ml with boiled pyrogen-free water. The solution is filtered, filled into 1,000 ampoules at the rate of 2 ml, and sterilised.

An ampoule with 2 ml contains 50 mg of active substance in the form of the hydrochloride.

d. 50 g of [o-(2,6-dichloroanilino)-phenyl]-acetic acid (2-pyridyl)-methyl ester and 1,950 g of finely ground suppository base composition (for example cacao butter) are thoroughly mixed and then fused. 1,000 suppositories each weighing 2.0 g are cast from the melt, which is kept homogeneous by stirring. The suppositories each contain 50 mg of active substance.

e. 60 g of polyoxyethylene sorbitane monostearate, 30 g of sorbitane monostearate, 150 g of paraffin oil and 120 g of stearyl alcohol are fused together, 50 g of [o-(2-methyl-6-chloro-anilino)-phenyl]-acetic acid 4-pyridyl-methyl ester are added and the mixture is amulsified in 590 ml of water which has been prewarmed to 40°C. The emulsion is stirred until it has cooled to room temperature and is filled into tubes.

f. The following formulation, for example, is used for the manufacture of anti-sunburn creams:

| | |
|---|---|
| [o-(2-Methyl-6-chloro-anilino)-phenyl]-acetic acid (2-pyridyl)-methyl ester | 1.0 g |
| Paraffin oil, low viscosity | 1.0 g |
| Polyoxyethylene-sorbitane monostearate | 2.0 g |
| Polyoxyethylene-sorbitol-lanoline derivative | 1.5 g |
| Sorbitol, 70% solution | 3.0 g |
| Stearic acid | 15.0 g |
| Preservative + perfume | q.s. |
| Water | ad. 100.0 g |

The examples which follow illustrate the manufacture of the new compounds but in no way represent the sole embodiment thereof.

EXAMPLE 1

[o-(2,6-Dichloro-anilino)-phenyl]-acetic acid (2-pyridyl)-methyl ester

To a solution of 33.0 g of 2-chloromethyl-pyridine hydrochloride in 350 ml of anhydrous dimethylformamide is added 8.7 g of sodium hydride-mineral oil suspension (50% strength). The suspension is stirred for 15 minutes at room temperature and is then added dropwise to a solution of 64.0 g of the sodium salt of [o-(2,6-dichloro-anilino)-phenyl]-acetic acid in 300 ml of anhydrous dimethylformamide. The mixture is stirred for 6 hours at 60°C, cooled and poured onto 2,000 ml of ice. The mixture is extracted 4 times with 1,000 ml of ether at a time. The combined ether extracts are extracted with 400 ml of 2 N-hydrochloric acid and the hydrochloric acid extract is separated off and rendered alkaline with concentrated sodium hydroxide solution at 0°C, whilst stirring. The suspension is extracted with 2,000 ml of ether and the ether extract is washed with 100 ml of water, dried over magnesium sulphate and evaporated to dryness at 40°C under 11 mm Hg. The residue is twice crystallised from ether-petroleum ether. [o-(2,6-Dichloro-anilino)-phenyl]-acetic acid (2 -pyridyl)-methyl ester melts at 80°–81°C.

Analogously to Example 1, [o-(2-methyl-6-chloro-anilino)-phenyl]-acetic acid (2-pyridyl)-methyl ester of melting point 80°–82°C (from ether-petroleum ether) is obtained starting from 63.0 g of the potassium salt of [o-(2-methyl-6-chloro-anilino)-phenyl]-acetic acid (melting point 290°–295°C) and 33.0 g of 2-chloromethyl-pyridine hydrochloride.

Analogously to Example 1, [o-(3-methyl-(2,6-dichloro-anilino)-phenyl]-acetic acid (2-pyridyl)-methyl ester of melting point 78°–80°C (from ether-petroleum ether) is obtained starting from 32.0 g of the sodium salt of [o-(3-methyl-2,6-dichloro-anilino)-phenyl]-acetic acid (melting point 287°–289°C) and 18.0 g of 2-chloromethyl-pyridine hydrochloride.

Analogously to Example 1, [o-(2,6-dichloro-anilino)-phenyl]-acetic acid (3-pyridyl)-methyl ester of melting point 78°–80°C (from ether) is obtained starting from 64.0 g of the sodium salt of [o-(2,6-dichloro-anilino)-phenyl]-acetic acid and 33.0 g of 3-chloromethyl-pyridine hydrochloride.

Analogously to Example 1 [o-(2-methyl-6-chloro-anilino-phenyl]-acetic acid (3-pyridyl)-methyl ester of melting point 89°–91°C (from ether) is obtained starting from 21.0 g of the sodium salt of [o-(2-methyl-6-chloro-anilino)-phenyl]-acetic acid and 11.0 g of 3-chloromethyl-pyridine hydrochloride.

Analogously to Example 1 [o-(2,6-dichloro-anilino)-phenyl]-acetic acid (4-pyridyl)-methyl ester of melting point 121°–123°C (from ethyl acetate) is obtained starting from 69.6 g of the sodium salt of [o-(2,6-dichloro-anilino)-phenyl]-acetic acid and 35.9 g of 4-chloromethyl-pyridine hydrochloride.

EXAMPLE 2

[o-(2-Methyl-6-chloro-anilino)-phenyl]-acetic acid (2-pyridyl)-methyl ester

A mixture of 1.0 g of [o-(2-methyl-6-chloro-anilino)-phenyl]-acetic acid, 15 ml of 2-hydroxymethyl-pyridine and 15 ml of anhydrous toluene is treated with 2 drops of concentrated sulphuric acid. The solution is heated to 130°C for 1 hour, during which the resulting water is distilled off azeotropically with the toluene. A further 20 ml of anhydrous toluene are added and again distilled off. The solution is then poured onto 150 g of ice. The mixture is twice extracted with 50 ml of ether at a time. The combined ether extracts are shaken with 15 ml of 2 N-hydrochloric acid at 5°C. The hydrochloric acid solution is separated off and rendered alkaline with 2 N-sodium hydroxide solution at 5°C. The suspension is extracted with 50 ml of ether and the ether solution is separated off, washed with 10 ml of water, dried over magnesium sulphate and evaporated to dryness under 0.1 mm Hg at 40° C. The residue is crystallised from ether-petroleum ether. [o-(2-methyl-6-chloro-anilino)-phenyl]-acetic acid (2-pyridyl)-methyl ester melts at 80°–82°C.

EXAMPLE 3

[o-(2,6-Dichloro-anilino)-phenyl]-acetic acid-3-(4-pyridyl)-propyl ester

A solution of 29.6 g of [o-(2,6-dichloro-anilino)-phenyl]-acetic acid, 30.0 g of dimethyl formamide-dineopentylacetal (1,1-dineopentyloxy-trimethylamine) and 15.0 g of 4-(3-hydroxypropyl)-pyridine in 900 ml of methylene chloride and 100 ml of ether are stirred under nitrogen for 6 days at room temperature. The solvent is then distilled off under 12 Torr. The residue is treated with 150 ml of ether and the undissolved [o-(2,6-dichloro-anilino)-phenyl]-acetic acid is separated. The filtrate is extracted with 50 ml of water, 40 ml of saturated aqueous sodium hydrogen carbonate solution, twice with 40 ml of water and subsequently twice with 40 ml of 2 normal hydrochloric acid. The combined hydrochloric acid extracts are made alkaline with 2 normal potassium hydrogen carbonate solution with the addition of ice. The precipitated oil is extracted with 200 ml of ether. The ethereal solution is washed twice with 30 ml of water, dried over magnesium sulphate, and evaporated under 11 Torr. The residue is crystallised from ether/petroleum ether. The [o-(2,6-dichloro-anilino)-phenyl]-acetic acid-3-(4-pyridyl)-propyl ester melts at 85°–86°C.

In analogous manner [o-(2,6-dichloro-anilino)-phenyl]-acetic acid-2-(2-pyridyl)-ethyl ester with a melting point of 67°–68°C (crystallisation from petroleum ether) is obtained starting from 2.96 g of [o-(2,6-dichloro-anilino)-phenyl]-acetic acid, 3.0 g of dimethyl formamide-dineopentylacetal, and 1.4 g of 2-(2-hydroxyethyl)-pyridine.

EXAMPLE 4

[o-(2,6-Dichloro-anilino)-phenyl]-acetic acid-(2-pyridyl)-methyl ester

While stirring, a mixture of 10 ml of oxalyl chloride and 20 ml of anhydrous benzene is added at 5°–10°C to a suspension of 10.0 g of the sodium salt of [o-(2,6-dichloro-anilino)-phenyl]-acetic acid in 100 ml of anhydrous benzene. The reaction mixture is then stirred for 3 hours at room temperature and the suspension is concentrated to dryness at 40°C and 11 Torr. The residue is treated with 40 ml of anhydrous benzene and the mixture is concentrated to dryness under 11 Torr. The residue, [o-(2,6-dichloro-anilino)-phenyl]-acetic acid chloride contaminated with sodium chloride, is treated with 50 ml of anhydrous benzene and, with stirring, subsequently with 2.5 g of 2-hydroxymethyl-pyridine at 10°C. The mixture is stirred for 1 hour at room temperature and concentrated at 40°C/11 Torr. the residue is treated with 150 ml of ether and 30 ml of 2 normal hydrochloric acid. The hydrochloric acid solution is isolated and shaken twice with 50 ml of ether and then made alkaline with 2 normal sodium hydroxide solution. The precipitated oil is dissolved in 50 ml of ether, the ether phase washed twice with 10 ml of water, dried over magnesium sulphate, and concentrated under 11 Torr at 40°C. The residue, [o-(2,6-dichloro-anilino)-phenyl]-acetic acid-(2-pyridyl)-methyl ester, is crystallised from ether/petroleum ether; m.p. 80°–81°C.

EXAMPLE 5

[o-(2,6-Dichloro-anilino)-phenyl]-acetic acid-3-(4-pyridyl)-propyl ester hydrochloride While stirring, 10 ml of 2 normal ethereal hydrochloric acid are added dropwise to a solution of 4.2 g of [o-(2,6-dichloro-anilino)-phenyl]-acetic acid-3-(4-pyridyl)-propyl ester (cf. Example 3) in 100 ml of anhydrous ether. The precipitated crystals are filtered off and recrystallised from ethanol/ether. The [o-(2,6-dichloro-anilino)-phenyl]-acetic acid-3-(4-pyridyl)-propyl ester hydrochloride melts at 166°–170°C.

EXAMPLE 6

[o-(2,6-Dichloro-anilino)-phenyl]-acetic acid-3-pyridyl ester

In an atmosphere of nitrogen and under anhydrous conditions, 0.62 g of 3-hydroxy-pyridine are heated with 10 ml of benzene and 2.6 ml of trifluoroacetic anhydride for 7 hours to reflux temperature. The mixture is evaporated in vacuo at a maximum temperature of 40°C, then 40 ml of absolute benzene are added and evaporation in vacuo is once more performed. The resulting yellow oil weighs 1.9 g and consists of crude 3-trifluoroacetoxypyridine in the form of the salt with trifluoroacetic acid.

This salt is stirred under nitrogen and anhydrous conditions for 1 hour with 6.5 ml of pyridine and 1.5 g of [o-(2,6-dichloro-anilino)-phenyl]-acetic acid at 20°–30°C and the mixture is then evaporated in vacuo at a maximum temperature of 40°C. The residue is dissolved in 50 ml of ether and while cooling with ice, washed with saturated potassium hydrogen carbonate solution, 1 N-hydrochloric acid, and with ice water. The bulk of the [o-(2,6-dichloro-anilino)-phenyl]-acetic acid-3-pyridyl ester remains in the ether layer and, after this latter has been dried with magnesium sulphate and evaporated in vacuo, is obtained therefrom as a pale brown oil which crystallises on trituration. The new ester contains as impurity 1-(2,6-dichloro-phenyl)-2-hydroxy-indole from which it can be separated by being dissolved in ether/petroleum ether 1:1 and filtered through a silica gel column. The [o-(2,6-dichloro-anilino)-phenyl]-acetic acid-3-pyridyl ester is obtained from the filtered ether/petroleum ether solution (evaporation in vacuo) in the form of colourless crystals which, after precipitation with petroleum ether from an ethereal solution, melt at 84°–86°C.

The above isolation proceeds with somewhat better yield if extraction of the ethereal solution with hydrochloric acid is dispensed with.

We claim:

1. A pharmaceutical anti-inflammatory and analgesic preparation, comprising an anti-inflammatory and analgesically effective amount of an ester of the formula

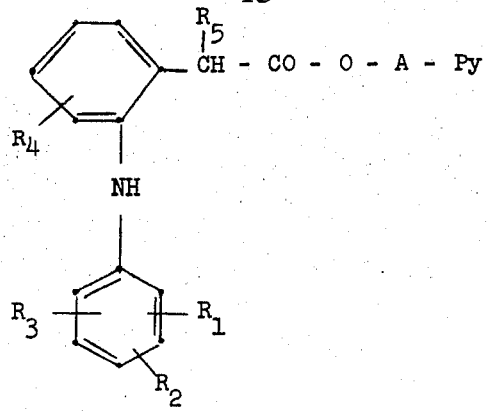

in which $R_1$ represents lower alkyl, lower alkoxy, halogen up to and including atomic number 35 or trifluoromethyl, $R_2$ represents hydrogen or a substituent corresponding to the definition of $R_1$, $R_3$ represents hydrogen, lower alkyl, lower alkoxy, halogen up to and including atomic number 35, $R_4$ represents hydrogen, lower alkyl, lower alkoxy, halogen up to and including atomic number 35 or trifluoromethyl, $R_5$ represents hydrogen, lower alkyl or benzyl, A represents a direct bond, lower alkylene or lower alkylidene and Py represents unsubstituted, lower alkyl-substituted or lower alkoxy-substituted pyridyl, wherein "lower" denotes said straight-chain radicals with up to 4 carbon atoms; the N-oxide or a pharmacologically tolerable acid addition salt thereof, together with a pharmaceutical excipient.

2. A composition as claimed in claim 1, wherein $R_1$ is in the 2-position of the anilino group and has the meaning chlorine or methyl, $R_2$ is in the 3- or 6-position and is hydrogen, chlorine or methyl, $R_3$ denotes hydrogen or, if $R_2$ is in the 6-position, also denotes a 3-methyl group, each of $R_4$ and $R_5$ represents hydrogen, A is a direct bond or methylene, ethylene, ethylidene, 1,2- or 1,3-propylene or 1,1-propylidene and Py is 2-, 3- or 4-pyridyl.

3. A composition as claimed in claim 1, in which the ester is [o-(2,6-dichloro-anilino)-phenyl]-acetic acid (2-pyridyl)-methyl ester.

4. A composition as claimed in claim 1, in which the ester is [o-(3-methyl-(2,6-dichloro-anilino)-phenyl]-acetic acid (2-pyridyl)-methyl ester or a pharmacologically tolerable acid addition salt thereof.

5. A composition as claimed in claim 1, in which the ester is [o-(2,6-dichloro-anilino)-phenyl]-acetic acid (3-pyridyl)-methyl ester or a pharmacologically tolerable acid addition salt thereof.

6. A composition as claimed in claim 1, in which the ester is [o-(2,6-dichloro-anilino)-phenyl]-acetic acid (4-pyridyl)-methyl ester or a pharmacologically tolerable acid addition salt thereof.

7. A composition as claimed in claim 1, in which the ester is [o-(2,6-dichloro-anilino)-phenyl]-acetic acid 2-(2-pyridyl)-ethyl ester or a pharmacologically tolerable acid addition salt thereof.

8. A composition as claimed in claim 1, in which the ester is [o-(2,6-dichloro-anilino)-phenyl]-acetic acid-3-pyridyl ester or a pharmacologically tolerable acid addition salt thereof.

9. A method for producing an anti-inflammatory effect in a mammal in need thereof, which comprises administering to said mammal an anti-inflammatory effective amount of a composition claimed in claim 1.

10. A method for producing an analgesic effect in a mammal in need thereof, which comprises administering to said mammal an analgesically effective amount of a composition as claimed in claim 1.

* * * * *